United States Patent [19]

Sitko

[11] Patent Number: 5,328,477
[45] Date of Patent: Jul. 12, 1994

[54] LIQUID INFUSION SYSTEM

[76] Inventor: Phillip M. Sitko, 4894 Mooncrest Dr., Corona, Calif. 91720

[21] Appl. No.: 80,087

[22] Filed: Jun. 21, 1993

[51] Int. Cl.$^5$ .............................................. A61M 5/20
[52] U.S. Cl. .................................. 604/134; 604/214; 222/103
[58] Field of Search ............... 604/131, 132, 134, 214, 604/246, 248; 128/DIG. 12; 222/95, 96, 103

[56] References Cited

U.S. PATENT DOCUMENTS

| | | | |
|---|---|---|---|
| 3,084,722 | 4/1963 | Klingerman | 141/362 |
| 3,595,232 | 8/1968 | Leibinsohn | 128/214 |
| 3,734,351 | 5/1973 | Gaudin | 604/134 |
| 3,902,635 | 9/1975 | Jinotti | 222/103 |
| 4,337,769 | 7/1982 | Olson | 128/214 |
| 4,447,232 | 5/1984 | Sealfon et al. | 604/134 |
| 4,504,267 | 3/1985 | Parmelee et al. | 604/134 |
| 4,557,728 | 12/1985 | Sealfon et al. | 604/134 |
| 4,781,689 | 11/1988 | Sealton et al. | 604/134 |
| 5,061,243 | 10/1991 | Winchell et al. | 604/132 |

Primary Examiner—John D. Yasko
Assistant Examiner—Anthony Gutowski
Attorney, Agent, or Firm—Harvey S. Hertz

[57] ABSTRACT

A liquid infusion system includes a flexible, flat, collapsible bag for storing liquid. An outlet communicates with the bag and a valve is used to control liquid outflow through the outlet tube. A rigid housing encloses the bag with the outlet tube projecting therefrom. A spring biased rigid pivot plate is positioned within the housing. The plate exerts pressure on the bag, tending to urge the bag toward a flat collapsed position and to expel liquids through the outlet when any liquid is present in the bag. Spring members are positioned in wells formed in the housing and the plate. The spring members exert a force against the plate.

3 Claims, 3 Drawing Sheets

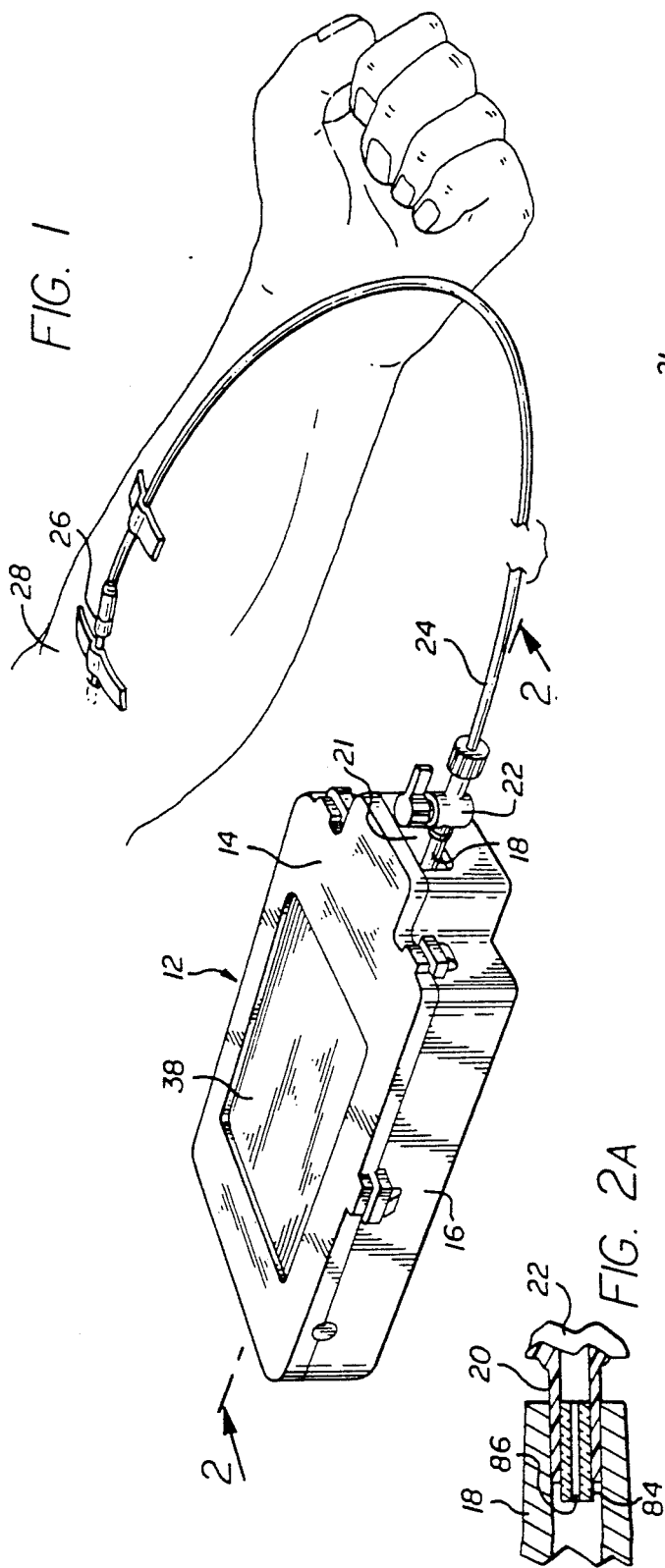
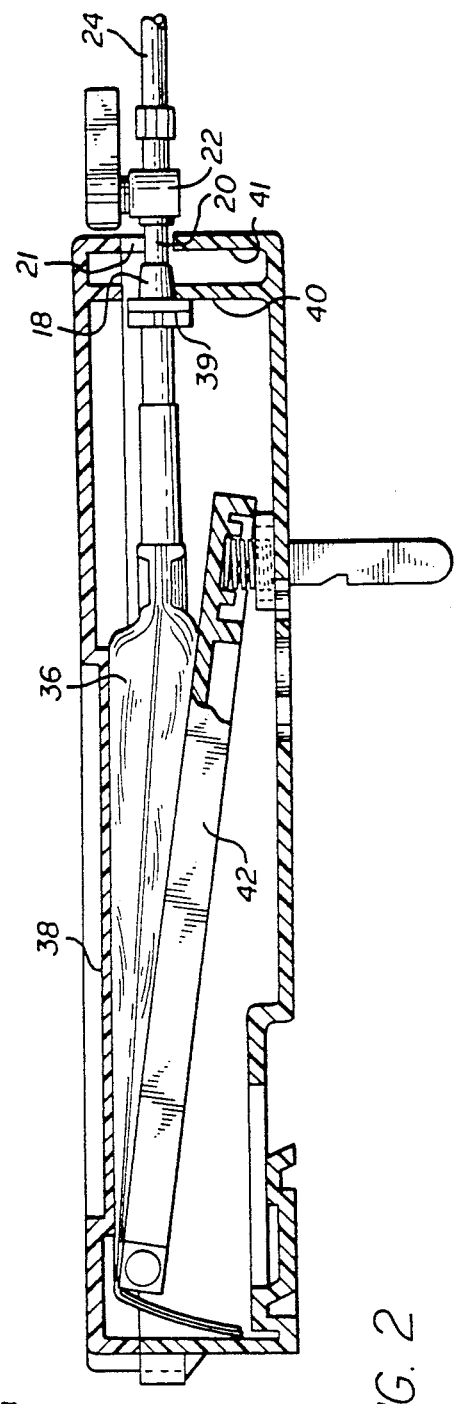
FIG. 1
FIG. 2A
FIG. 2

LIQUID INFUSION SYSTEM

BACKGROUND OF THE INVENTION

1. Field of the Invention

The field of art to which the invention pertains includes the field of liquid infusion systems, and more particularly, to an infusion system having a spring loaded plate for collapsing a bag containing liquid as to aid the flow of liquid without the need for gravity to provide the impetus for the discharge of fluid in the bag.

2. Description of the Prior Art

Apparatus for pressure infusion of blood and parenteral solutions are well known. Pressurized infusion of parenteral solutions and blood is desirable in circumstances where the infusion can be performed independent of gravity. For example, the infusion must be performed at an accelerated rate under emergency conditions or to allow a patient to function while the solution is being administered.

U.S. Pat. No. 4,337,769 utilizes a flexible cellular material to apply pressure to a bag of fluid.

U.S. Pat. No. 3,595,232 utilizes a substantially rectangular container containing a moveable plate which applies pressure to a bag of fluid from the force of an externally located biasing mechanism.

U.S. Pat. No. 4,504,267 utilizes one or more pressure plates which through the use of springs of varying configuration applies pressure to a bag of fluid.

Other known patents include U.S. Pat. Nos. 4,557,728; 4,447,232; 4,781,689; and 3,084,722.

In order to overcome the attendant disadvantages of prior art apparatus which pressure infuse blood and parenteral solutions, the present invention utilizes a simple, yet successful, structure for applying a force to the liquid containing bag. Further, the device may be pre-loaded so that when liquid is to be infused, a simple release mechanism is utilized to commence the flow of liquid.

SUMMARY OF THE INVENTION

A parenteral liquid infusion system includes a flexible, flat, collapsible bag having an outlet communicating with the bag. A valve is utilized to control liquid outflow through the outlet tube. A rigid housing encloses the bag with the outlet tube projecting outwardly therefrom. A spring biased rigid pivot plate is positioned within the housing and exerts a pressure on the bag, tending to urge the bag toward its flat collapsed position and to expel liquid through the outlet tube when liquid is present in the bag. Spring members are positioned in wells formed in the housing and the plate. The spring members exert a force against the plate and, hence, exert pressure on the plate. A pre-loading arm can be attached to the pivot plate. The pre-loading arm compresses the springs minimizing the plate from exerting a force against the bag. Release of the pre-loading arm when in its first position enables the springs to exert a force against the pivot plate and, hence, the bag when the pre-loaded arm is moved from the first position.

The advantages of this invention, both as to its description and mode of operation, may best be understood by reference to the following detailed description taken in connection with the accompanying drawings, wherein like reference numerals designate like parts throughout the figures.

BRIEF DESCRIPTION OF THE DRAWINGS

FIG. 1 is a perspective view of the liquid infusion system connected to an arm of a patient.

FIG. 2 is a cross-sectional view of the liquid infusion system taken along the line 2—2 of FIG. 1.

FIG. 2a is a partial cross-sectional view of the interconnection of the system stop cock and the liquid bag.

DESCRIPTION OF THE PREFERRED EMBODIMENT

Figure 3:
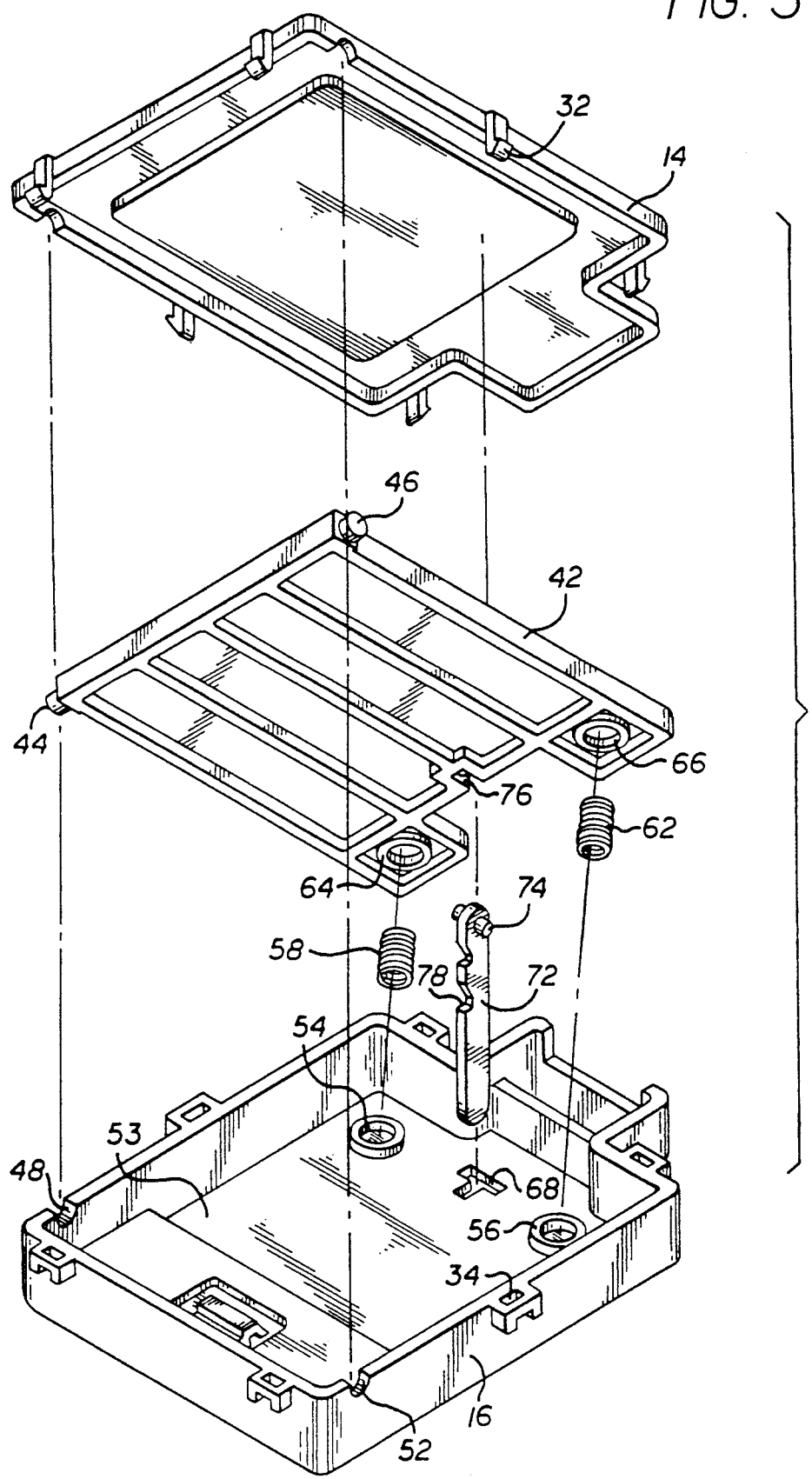
FIG. 3 is an exploded perspective view of the housing of the liquid infusion system.

Referring now to the drawings, there is shown in FIG. 1 a parenteral liquid infusion system which is used to pressure infuse solutions as well as blood into a patient's arm. A pressure infusion module 12 comprises a rigid housing containing a flexible, collapsible bag (not shown in FIG. 1) for the liquid. The housing includes a cover plate 14 and a lower container member 16. A conventional tubing 18, is connected from the bag in the housing through an opening 21 formed in the lower container 16 to a connector tube 20 of a stop cock 22, which in turn is connected through a main tubing 24 to a catheter 26 inserted in the arm 28 of a patient. When in operation and with the stop cock 22 in the open position, fluid from the bag will flow through the tubing 18 and 24 to the catheter 26 and into the arm 28 of the patient.

Referring now to FIGS. 2 and 3, the pressure infusion module 12 is shown in greater detail. A plurality of tangs 32 are formed along the periphery of the cover plate 14 and mate with slots 34 formed on the periphery of the lower container 16., The flexible collapsible bag 36 is positioned directly below a recessed top surface 38 of the cover plate 14. A finger guard 39 is formed in the tubing 18 and is positioned to rest against one of the transverse flanges 40 or 41 formed in the lower container 16.

The bag 36 rests on a pressure plate 42, which is positioned in the lower container 16. As can be clearly seen, the recessed top surface 38 of the cover plate 14 and the pressure plate 42 together can exert a force on the fluid in the bag 36 so that the fluid in the bag will flow into the tubing 18 when the stop cock 22 is open.

To enable the pressure plate 42 to exert a force on the bag 36 and its contents, the pressure plate is pivotally mounted at one end so that a pair of rods 44 and 46 at the pivot end of the pressure plate 42 mate in pivot slots 48, 52, respectively, which are formed in the top peripheral surface of the lower container 16. The lower interior surface of the lower container at the end opposite to the pivot slot end contains spring wells 54 and 56. The wells 54 and 56 have one end of a pair of freely mounted springs 58 and 62 positioned therein, with the other end of the springs positioned in a second pair of spring wells 64. 66, respectively, formed in the bottom surface of the pressure plate 42. Thus, with the springs 58 and 62 exerting an upward force on the pressure plate 42, this force, in turn, exerts a force on the fluid in the collapsible bag 36.

A T-shaped slot 68 is formed in the bottom surface of the lower container 16 and a pre-loading arm 72 extends therethrough. The arm 72 contains a transverse horizontal rod 74 at the interior end thereof, which is connected to a slot 76 formed in the pressure plate 42 intermediate the spring wells 64 and 66. The pre-loading arm 72 further contains a plurality of notches 78 which lock in the bottom well 53 adjacent the T-shaped slot 68, enabling the pressure plate to be locked in a position shown in FIG. 2.

Figure 4:
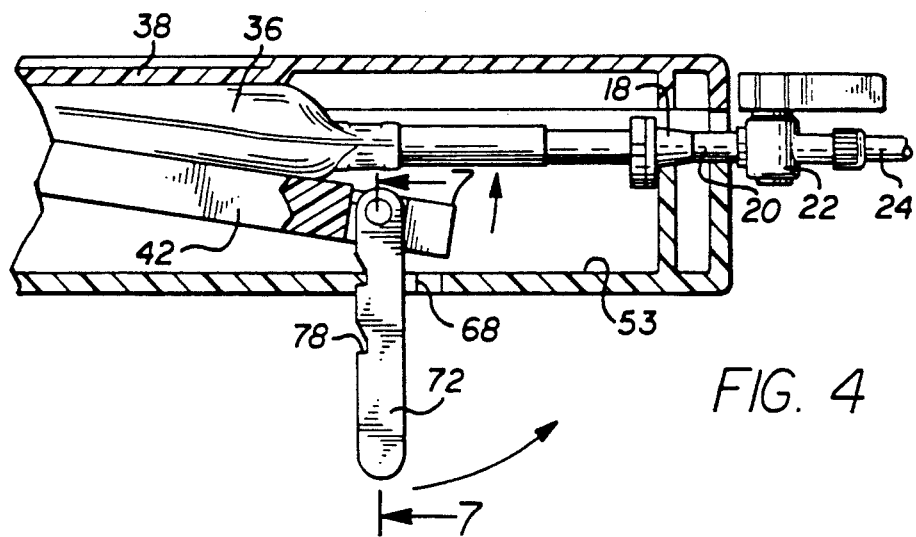
FIG. 4 is an enlarged partial cross-sectional view of the right end of the housing of FIG. 3.
Figure 5:
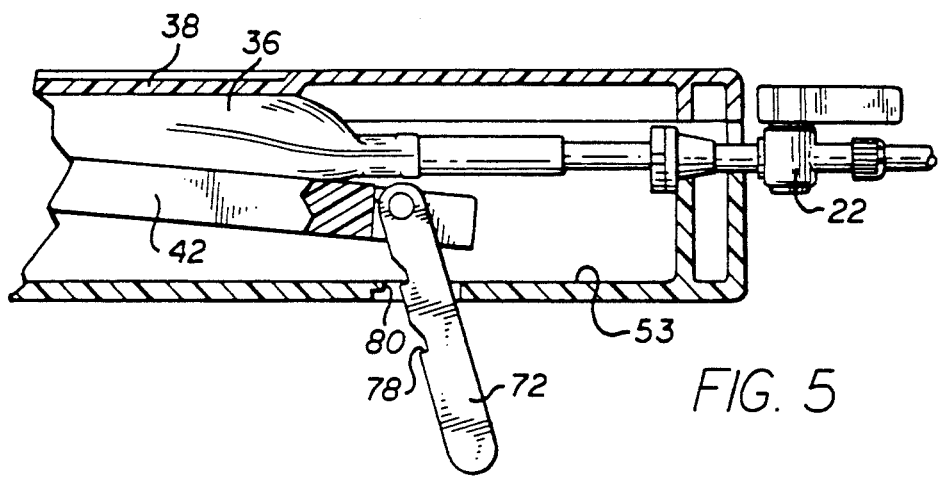
FIG. 5 is an enlarged partial cross-sectional view of the right end of the system of FIG. 4 illustrating an alternative position thereof.

As illustrated in FIG. 4, with the pre-loading arm 72 positioned as shown in FIG. 2, the pressure plate 42 exerts a minimal, if any, force on the fluid contained in the collapsible bag 36. When the pre-loading arm 72 is moved to the right in the direction of the arrow as shown in FIG. 4, the pre-loading arm is released from the lip 80 which abuts the pre-loading arm notch 78, enabling the pre-loading arm as well as the pressure plate 42 to move upwardly in FIGS. 2, 4 and 5, exerting a force due to the compressed springs 58 and 62, acting upwardly on the pressure plate 42. Thus, fluid will flow from the collapsible bag 36, irrespective of gravity.

Figures 6, 7:
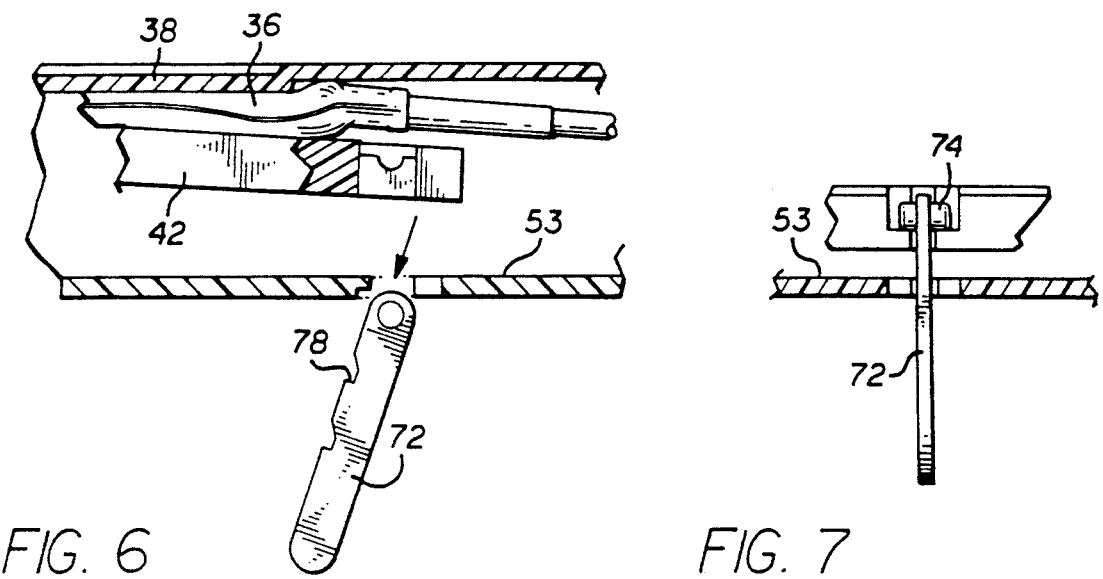
FIG. 6 is an enlarged partial view illustrating removal of a portion of the pre-loading mechanism.
FIG. 7 is an end view of the device taken along the line 7—7 of FIG. 4.

As shown in FIG. 6, once the collapsible bag is feeding fluid to the catheter 26, the pre-loading arm 72, which extends through the bottom surface of the lower container 26 can be removed as the T shaped slot 68 can also accommodate the horizontal rod 74.

The liquid infusion system is designed to infuse the contents of the collapsible bag 36 at a predetermined rate. To control the flow of fluid, a glass tube 84 shown in FIG. 2a, is positioned in the connector tube 20. The tube 84 has a fixed orifice 86 whose diameter controls the flow of fluid. In addition, the springs 58 and 62 generate compression on the collapsible bag 36 forcing the fluid in the bag to flow. By adjusting the compression of the springs as well as the size of the orifice 86, it has been found that an infusion time of 33 minutes for a 50 milliliter bag or 60 minutes for a 100 milliliter bag would be satisfactory.

The present invention of utilizing the glass tube at a preset orifice 86 as well as the springs 58 and 62 replaces a roller clamp which is adjusted to adjust the flow of fluid in the main tubing 24.

It should be noted that the lower container 16 has a belt clip 82 formed therein for enabling a patient to wear the module 12 and to walk around during the infusion process.

I claim:

1. A liquid infusion system comprising:
   a flexible, flat, collapsible bag for storing liquid and an outlet tube for communicating with said bag, valve means to control liquid outflow through said outlet tube;
   a rigid housing enclosing said bag with said outlet tube projecting outwardly therefrom and having a slot formed therein;
   a spring biased rigid pivotal plate pivotally mounted and positioned within said housing and exerting pressure on said bag tending to urge said bag toward a flat collapsed position and to channel liquid through said outlet when liquid is present in said bag, said pivot plate being planar in configuration and having a slot formed therein;
   spring members positioned in wells formed in said hosing and said plate, said spring members exerting a force against said plate, said pivotal plate slot being formed intermediate said plate wells; and
   a pre-loading arm having an interior end extending into said housing and releasably connected to said housing intermediate said interior end, said arm being connected to said housing in a first position and disconnected from said housing in a second position, said arm being attached to said pivot plate, said pre-loading arm compressing said springs and minimizing said plate from exerting a force against said bag when said pre-loading arm is in said first position, and enabling said springs to exert a force against said pivot plate and, hence, said bag when said pre-loading arm is in said second position, said pre-loading arm containing a transverse horizontal rod at the interior end thereof which is connected to said slot formed in said pressure plate, said arm containing at least one notch releasably locking said pre-loading arm in said housing slot.

2. A liquid infusion system in accordance with claim 1 wherein a glass tube is positioned intermediate said bag and said valve means, said glass tube having a fixed orifice for controlling the flow of fluid from said bag.

3. A liquid infusion system in accordance with claim 1 where said pre-loading arm has a longitudinally extending axis which extends through said hosing and attaches to said pivot plate generally perpendicular to the plane of said pivot plate.

* * * * *